United States Patent [19]

Mazur et al.

[11] Patent Number: 5,220,009

[45] Date of Patent: Jun. 15, 1993

[54] PHENOTHIAZINIUM SALTS AND THEIR USE FOR DISINFECTING AQUEOUS EFFLUENTS

[75] Inventors: Yehuda Mazur, Rehovot; Aureliu Acher, Ramat-Gan; Lea Shragina; Moshe Avramoff, both of Rehovot, all of Israel

[73] Assignee: Yeda Research and Development Company Limited, Rehovot, Israel

[21] Appl. No.: 691,313

[22] Filed: Apr. 25, 1991

[30] Foreign Application Priority Data

May 3, 1990 [IL] Israel ........................ 94275
Jun. 7, 1990 [IL] Israel ........................ 94663

[51] Int. Cl.⁵ ................ C07D 207/00; C07D 209/00; C07H 15/00; C07H 17/00
[52] U.S. Cl. .................... 536/174; 536/55; 548/405
[58] Field of Search ............ 536/17.4, 55; 548/405

[56] References Cited

U.S. PATENT DOCUMENTS 4,916,711 4/1990 Boyer et al. ................ 372/53

Primary Examiner—Ronald W. Griffin
Attorney, Agent, or Firm—Helfgott & Karas

[57] ABSTRACT

Novel 3,7-disubstituted phenothiazinium salts are active in the photochemical disinfection of aqueous effluents. The novel salts are of the general formula

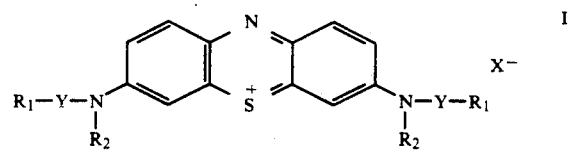

wherein:
either $R_1$ is a saccharide residue;
$R_2$ is alkyl, cycloalkyl, aryl, aralkyl or heterocyclyl, any alkyl or alkylene chain being optionally interrupted by one or more heteroatoms, and Y is alkylene optionally substituted by alkyl, cycloalkyl, aryl or aralkyl; or
$R_1$ and $R_2$ are each methyl and Y is a bond; and when $R_1$ is a saccharide residue X is an anion selected from halogen, $R_3CO_2^-$, $R_3SO_3^-$ and $R_3OSO_3^-$, wherein $R_3$ is alkyl, cycloalkyl, aryl, aralkyl or heterocyclyl, and
when $R_1$ and $R_2$ are each methyl, X is an anion selected from $R_3SO_3^-$, $R_3OSO_3^-$ wherein $R_3$ is as defined above and $R_4CO_2^-$, wherein $R_4$ is an aldose or ketose residue, an N-protected α-amino acid residue or a ω-carboxy-α-amino acid residue.

15 Claims, No Drawings

PHENOTHIAZINIUM SALTS AND THEIR USE FOR DISINFECTING AQUEOUS EFFLUENTS

BACKGROUND OF THE INVENTION

This invention relates to novel organic dyes which are active in the photochemical disinfection of effluents. Sewage effluents of domestic, agricultural or other origins contain large amounts of microbiological pollutants which are not destroyed by treatment in activated sludge plants. Therefore, water resulting from such treatment is unsuitable for human consumption or agricultural use and, after penetrating into ground water, gives rise to health and epidemiological hazards.

A photochemical procedure for disinfection of effluents consists of their treatment with small amounts of certain dyes in the presence of oxygen dissolved in the effluent and visible light (sun or artificial light). The dye absorbs the light energy and transfers it to the oxygen molecules which are then capable of destroying the microorganisms. Alternatively, the dye, after absorbing light energy, acts directly upon the microorganism leading to their annihilation.

The use of methylene blue as a dye in the photochemical disinfection of effluents is known. Thus, domestic sewage effluents which had been previously treated in activated sludge plants, have been disinfected by dissolving therein minute amounts (say 2 ppm) of methylene blue and subjecting the solution to visible light irradiation in the presence of air. However, the use of methylene blue in such disinfection processes is not fully satisfactory because of the tendency of this dye to be adsorbed by clays and soil components which are present in the aqueous effluent. This tendency can be ascribed perhaps to the high degree of dissociation of methylene blue. Another drawback of the use of methylene blue in the aforementioned process is its instability towards active oxygen species which are generated in the treated water in the course of the photochemical process.

SUMMARY OF THE INVENTION

The present invention relates to novel dyes which are methylene blue analogues and are more effective for disinfecting water and other effluents, such as domestic sewage effluents, than methylene blue itself.

The invention also provides methods for the preparation of these dyes. It further relates to their use as disinfectants in a method for disinfection of aqueous effluents.

DETAILED DESCRIPTION OF THE INVENTION

The present invention provides novel phenothiazinium salts of the general formula (I):

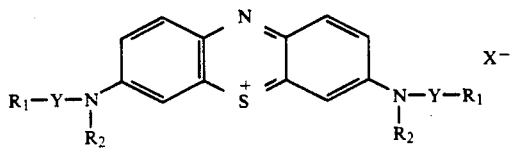

wherein:
either $R_1$ is a saccharide residue;
$R_2$ is alkyl, cycloalkyl, aryl, aralkyl or heterocyclyl, any alkyl or alkylene chain being optionally interrupted by one or more heteroatoms, and Y is alkylene optionally substituted by alkyl, cycloalkyl, aryl or aralkyl; or $R_1$ and $R_2$ are each methyl and Y is a bond; and when $R_1$ is a saccharide residue X is an anion selected from halogen, $R_3CO_2^-$, $R_3SO_3^-$ and $R_3OSO_3^-$, wherein $R_3$ is alkyl, cycloalkyl, aryl, aralkyl or heterocyclyl, and when $R_1$ and $R_2$ are each methyl, X is an anion selected from $R_3SO_3^-$, $R_3OSO_3^-$ wherein $R_3$ is as defined above and $R_4CO_2^-$, wherein $R_4$ is an aldose or ketose residue, an N-protected α-amino acid residue or a ω-carboxy-α-amino acid residue.

The saccharide residue may be derived from a monosaccharide, e.g. glucose, fructose, galactose, mannose, ribose etc., from a disaccharide, e.g. sucrose, lactose, maltose, etc., or from an oligosaccharide. Sugar derivatives, such as aminosugars, deoxysugars, etc., are also encompassed by the present invention.

In this invention, preferred hydrocarbyl radicals, as defined for $R_2$, Y and $R_3$ are $C_1$–$C_4$ alkyl, e.g. methyl, ethyl; $C_3$–$C_6$ cycloalkyl, e.g. cyclopropyl, cyclohexyl; $C_6$–$C_{10}$ aryl, e.g. phenyl, naphthyl; $C_7$–$C_{10}$ aralkyl, e.g. benzyl; and heterocyclyl, e.g. pyridyl, furyl, etc. All these radicals may be optionally substituted by radicals such as alkyl, halogen, amino, hydroxy, etc. The heteroatom that interrupts the alkylene chain of the alkyl or aralkyl radical of $R_2$ may be oxygen, sulfur or nitrogen.

It has been found in accordance with the invention that the novel salts of the above formula (I) are very effective for disinfection of aqueous sewage effluents and are free from the above discussed drawbacks of methylene blue, having a lower tendency to be adsorbed by clays and other soil components and they are further more stable than methylene blue towards active oxygen species produced in the treated water.

In another aspect, the invention also provides a process for disinfecting aqueous effluents which comprises dissolving in said effluents from 1 to 4 ppm of a salt of formula (I) above, and subjecting the solution to irradiation with white light in the presence of air.

For the preparation of some of the novel salts of formula (I) above, the inventors have also developed some new and more efficient methods than the prior art ones. The general method hitherto used for preparing bis(dimethylamino)phenothiazine-5-ium salts (hereinafter "BDAP salts") with organic acids, consisted in the treatment of methylene blue (formula I, $R_1=R_2=CH_3$, X=Cl) with the sodium, or other alkali metal salts of organic acids in an aqueous or alcoholic medium. The resulting salts with the organic acids could be separated by filtration or extraction with an organic solvent. The dodecyl sulfate and dodecyl benzenesulfonate BDAP salts, both of which are novel, could be prepared by the above described conventional method, namely by the reaction of methylene blue with an excess of sodium salt of dodecyl sulfate or dodecylbenzenesulfonate in an aqueous solution. The desired salts precipitated from the aqueous solution and were separated by decantation followed by extraction with chloroform.

However, the above described method was found to be unsuitable in many instances, especially where the BDAP salt to be prepared is water soluble. It was found by the inventors that in some cases a preferred method involves the reaction of methylene blue with the silver salt of the organic acid, the resulting in the precipitation of silver chloride. The organic BDAP salt can then be recovered from the water solvent, e.g. by lyophilization. In some cases, however, this method did not yield the desired product, because the silver chloride did not precipitate from the aqueous solution, but rather formed an occluded solution with the BDAP salt of the organic acid. In order to overcome this drawback, a new preparative method was developed, wherein the sulfate salt of BDAP was reacted with a barium salt of the organic acid and the desired salt of BDPA was recovered from the aqueous solution. The BDAP sulfate used in this method is novel and can be prepared by the reaction of methylene blue with silver sulfate in an aqueous or methanolic solution. In this manner, the salt of BDAP with glutamic acid was prepared.

BDAP p-toluenesulfonate (formula I, $R_1=R_2=CH_3$, $X=CH_3C_6H_5SO_3^-$) was prepared by reacting methylene blue with silver p-toluenesulfonate (prepared from p-toluenesulfonic acid and silver oxide in an aqueous or methanolic solution). The same method was used for the preparation of the gluconic acid salt of BDAP. The silver gluconate used in this preparation was obtained by reacting gluconolactone and silver acetate. preparation was obtained by reacting gluconolactone and silver acetate.

Phenothiazinium derivatives of formula I above in which $R_1$ is a saccharide residue, may be prepared by several processes, as exemplified by the synthesis of the following derivative (Ia):

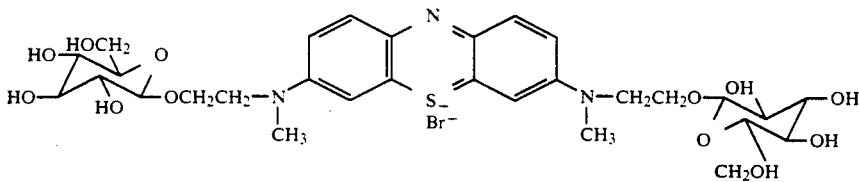

One process involves condensation of a methylamine derivative containing a glucosyl radical (II) with phenothiazinium perbromide (III) as follows:

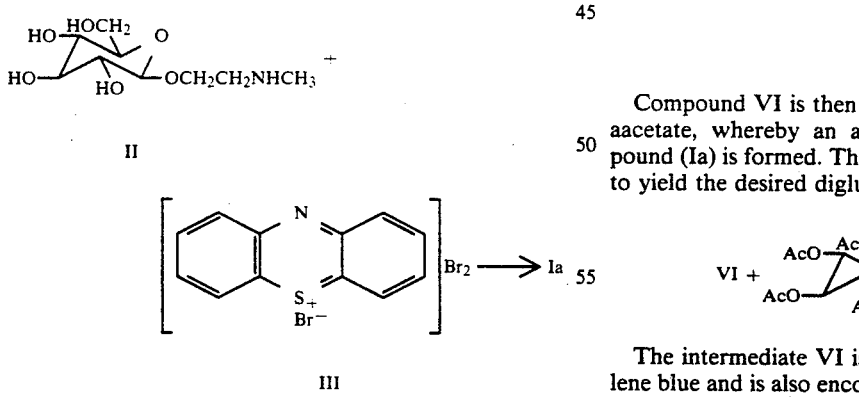

Compound II is prepared conveniently by the following sequence of reactions: N-methylaminoethanol (IV) is reacted with carbobenzoxy chloride, resulting in the carbobenzoxy derivative (V). The latter is condensed with α-D-acetylbromoglucose in the presence of mercuric cyanide, followed by hydrolysis of the acetate groups and deprotection of the carbobenzoxy function, by catalyzed hydrogenation, to give compound II:

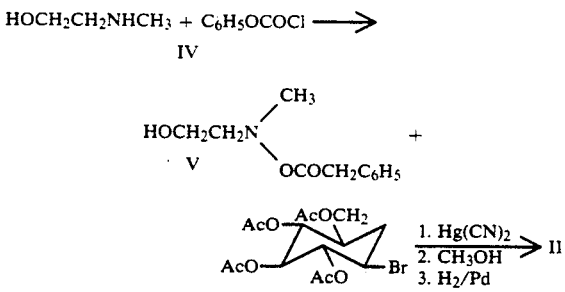

A second process for the preparation of compound Ia involves the intermediacy of a phenothiazinium derivative of formula VI, which is formed by the reaction of phenothiazinium perbromide (III) with N-methylaminoethanol (IV).

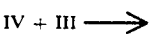

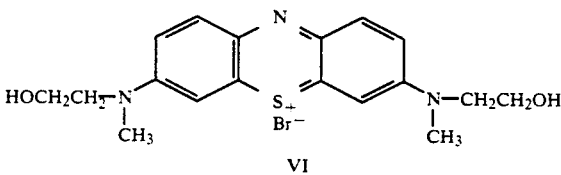

Compound VI is then condensed with glucose pentaacetate, whereby an acetylated derivative of compound (Ia) is formed. This material is then deacetylated to yield the desired diglucoside (Ia).

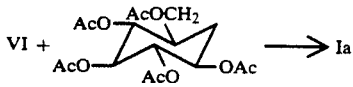

The intermediate VI is a novel derivative of methylene blue and is also encompassed by the present invention. It may be used as starting material for the preparation of other methylene blue derivatives.

Using analogous reaction schemes, other derivatives of the general formula I can be prepared. Thus, N-methylaminoethanol IV in both processes can be substituted by other amino alcohols of the general formula HO—Y—N(H)R$_2$. Its condensation with phenothiazinium perbromide (III) yields compounds of the general formula (VII):

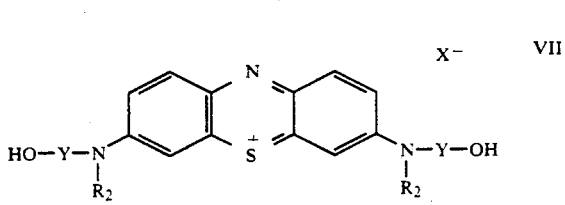

where $R_2$ and Y are as hereinbefore defined.

Compounds of the general formula (VII) can then be reacted with acetylated mono- or disaccharides or, alternatively, with acetylated α-D-bromo-mono or -disaccharides, to give the compounds of formula (I).

The novel salts of formula (I) above were tested for their photodynamic activity against test micro-organisms being non-mobile fecal coliform from sewage water, identified as *Escherichia coli*. This organism was subjected to photochemical disinfection in an isotonic solution of the sterilized effluent after addition of 2 ppm of the salts of formula (I) above and irradiation of the solution with white light. Samples of the solution were collected after different periods of irradiation and counted using the most probable number enumeration procedure.

EXAMPLE 1

3,7-Bis(dimethylamino)phenothiazin-5-ium p-methylbenzenesulfonate (Compound 1)

A solution of 2.8 g of silver p-methylbenzenesulfonate [N. Kornblum et al, J. Am. Chem. Soc. 81:4113 (1959)] in 200 mL of methanol was heated to 40° C. and then slowly added to a solution of 4.4 g (10 mmoles) of methylene blue (85% purity) in 200 mL of methanol at the same temperature. After being left for 24 hrs, the precipitated silver chloride was separated by centrifugation and washed with methanol. The clear methanolic filtrate and the washings were combined, evaporated to dryness and dried at 40° C. in vacuo to give 5.12 g of the crude product. Recrystallization from ethanol afforded 3.2 g of a product, m.p. ca. 250° C. (dec.).

NMR(d-MeOH):2.34(s,3H, Me-Ar); 7.1–7.8(m, 10H, aromatic H).

UV Spectrum $(H_2O)\lambda_{max}663$ nm($\epsilon = 7.0 \times 10^4$); $\lambda^{sh}419$ nm.

Anal. Calc. for $C_{23}H_{25}N_3S_2O_3.2H_2O(491.5)$: C,56.2; H,5.9; N,8.5; S,13.0. Found: C,55.6; H,5.4; N,8.4; S,12.8.

EXAMPLE 2

3,7-Bis(dimethylamino)phenothiazin-5-ium glutamate (Compound 2)

A solution of 0.75 g (2.25 mmoles) of silver sulfate in 70 mL of water at 50° C. was added with stirring to a solution of 2.2 g (5 mmoles) of methylene blue (85% purity) in 50 ml of water at the same temperature. On the next day the precipitated silver chloride was separated by centrifugation and washed with small amounts of water. The combined solutions contained 2.25 mmoles of BDAP sulfate $(C_{16}H_{18}N_3S)_2.SO_4$.

A mixture of 1.4 g (10 mmoles) of glutamic acid and 1.0 g (5 mmoles) of barium carbonate in 60 mL of water at 50° C. was stirred to give a clear solution which contained 5 mmoles of barium glutamate [Ba(C₅H₈NO₄)₂].

A solution of 2 mmoles of barium glutamate was added with stirring to the solution of 2.25 mmoles of BDAP sulfate at 50° C. On the next day the precipitated barium sulfate was separated by centrifugation and washed twice with small amounts of water. The combined filtrate and wash solutions were lyophilized to give 2.16 g of crude methylene blue glutamate.

UV Spectrum $(H_2O)\lambda_{max}665$ nm.

NMR (d-MeOH): 2.1–2.2 (m, CH—CH₂); 2.4–2.5 (m,CH₂CO₂); 3.6 (CH); 7.4–7.6 (m, aromatic H).

EXAMPLE 3

3,7-Bis(dimethylamino)phenothiazin-5-ium gluconate (Compound 3)

To a solution of 1.32 g (3 mmoles) of methylene blue (85%) in 50 mL of water at 50° C., there was added an aqueous suspension of 0.90 g (3 mmoles) of silver gluconate [H. A. Tajmir-Riahi; J. Inorg. Biochem.27: 205 (1986)] in 50 mL of water. The mixture was stirred for 15 min. at 70°–80° C. and overnight at room temperature. The precipitated silver chloride was separated by centrifugation and washed twice with small amounts of water. The residue obtained, 1.8 g, contains ca.20% silver chloride (by determined chlorine content).

NMR ($D_2O$): 3.2–3.8(m,CH-O); 5.1 (d,CH₂O); 7.0–7.2(m,aromatic H).

EXAMPLE 4

β-2(Methylamino)ethyl-D-glucopyranoside (Compound II)

A suspension of N-carbobenzoxy-N-methyl ethanolamine (V) (6.3 g, 30 mmols), molecular sieves 4 Å (1 g, powder), Hg(CN)₂(7.1 g, 28 mmols) and 40 ml of dry ethylene dichloride was stirred at room temperature for 2 h. then, 2,3,4,6-tetra-O-acetyl-α-D-glucopyranosyl bromide (10 g, 24 mmols) was added and the reaction mixture was left stirring overnight. NaHCO₃ (1 g), water and methylene chloride (50 mL) were added to the reaction mixture. The organic layer, after filtration, was washed with small amounts of water, dried over Na₂SO₄ and evaporated. The residue was flash-chromatographed on silica gel (EtOAc/CH₂Cl₂, 2:1:5). The product (4.5 g, 35%) was identified as N-carbobenzoxy-N-methylaminoethyl-2,3,4,6-tetra-O-acetyl-β-glucopyranoside.

This compound was hydrolyzed in methanol (100 mL) by treating with 2N sodium methoxide for 1 h, then neutralized with a few drops of alcoholic hydrogen chloride solution and hydrogenated, using 10% Pd (2 g) on charcoal, at 50 psi. The resulting mixture was filtered and evaporated to give compound 4 (1.97 g, 100%) as an anhydrous powder. Its structure was assigned by ¹³C NMR.

¹³C NMR ($D_2O$): δ35.8; 51.6; 63.6, 67.7; 72.5; 75.9, 78.5, 78.8, 105.0 ppm; $\alpha_D^{25} = -21.1$ (c=5, CH₃OH).

EXAMPLE 5

3,7-Bis(N-methyl-N-β-glucopyranosylethylamino)-phenothiazin-5 ium bromide (Compound Ia)

Phenothiazinium perbromide (III) (0.3 g, 0.68 mmols) was suspended in ethanol (20 mL) and treated with a solution of β-2-(methylamino)ethyl-D-glucopyranoside (⁴) obtained in Example 4, upon which the mixture turned blue. An aliquot of this mixture, diluted with ethanol (1:200), showed $\lambda_{max}$ at 654 nm, which is a characteristic of a diaminophenothiazinium chromophore. Chromatography on a silica gel column using, as an eluent, mixtures of CH₂Cl₂ and CH₃OH, 4:1, resulted in a blue product (70 mg, 14%) to which the structure (Ia) was assigned by ¹³C NMR spectrum.

$^{13}$C NMR (D$_2$O): δ42.5, 51.8, 63.9, 69.9, 72.7, 76.1, 78.7, 78.9, 105.5, 109.2, 121.7, 136.9, 139.5, 156.4, 156.6.

EXAMPLE 6

3,7-Bis(N-methyl-N-hydroxyethylamino)phenothiazin-5-ium bromide (Compound VI)

Freshly prepared phenothiazinium perbromide (III) (20 g) was quickly added to a magnetically-stirred solution of N-methyaminoethanol (25 g) in ethanol (500 mL) at room temperature. The reaction mixture was stirred overnight, then filtered and the blue precipitate was washed with ethanol v (3×50 mL), ether (until washing colorless), and methylene blue (until washing pale blue) to give 5.2 g (2% yield) of the phenothiazinium derivative (VI).

Anal. Calc. for C$_{18}$H$_{22}$BrN$_3$SO$_2$: C 50.94; H 5.25; N 9.9; S 7.59; Br 18.81. Found C 51.15; H 5.14; N 9.76; S 7.71; Br 18.72%.

$^{13}$C NMR (D$_2$O): δ156.3, 139.13, 136.7, 1221.6, 108.9, 61.58, 57.27, 42.4 ppm.

EXAMPLE 7

3,7-Bis(N-methyl-N-β-glucopyranosylethylamino)-phenothiazin-5-1um bromide (Ia)

The phenothiazinium derivative (6) of Example 3 (17 g) and pentaacetyl-α-D-glucopyranose (3.12 g) were dissolved in methylene chloride (100 mL) and cooled to −50° C. This solution was treated with trimethylsilyl trifluoromethanesulfonate (2 mL) dissolved in dichloromethane (20 mL) and stirred at room temperature for two hours. The methylene chloride solution was washed with sodium bicarbonate solution, then with water and dried on sodium sulfate. Evaporation of the solvent at reduced pressure resulted in a violet material which was dissolved in methanol (5 mL) and precipitated with ether (25 mL) to give 3.5 g of compound (Ia). This material was dissolved in 1 L dry methanol, treated with 10 mL of 4N sodium methoxide and left at room temperature for 0.5 hrs. The reaction mixture was neutralized using hydrogen bromide solution and then evaporated to dryness. The residue was dissolved in 5 mL of methanol acetic acid mixture (10:1) and flash chromatographed over a column of silica gel using the same solvent mixture to give 1.2 g of Ia, identical to the compound described above.

EXAMPLE 8

3,7-Bis(N-methyl-N-β-galactopyranosylylethylamino)-phenothiazin-5-1um bromide

By the same procedure as for Example 7 but using pentaacetyl-α-D-galactopyranose instead of pentaacetyl-α-D-glucopyranose, the title compound was obtained. Its structure was assigned by $^{13}$C NMR spectrum.

$^{13}$C NMR (D$_2$O): δ42.5, 55.7, 57.4, 64.0, 71.5, 73.7, 75.7, 78.1, 106.0, 131.8, 137.0, 139.4, 156.4, 156.6 ppm.

EXAMPLE 9

Bioassay Determination

25 μg of BDAP p-toluenesulfonate (compound 1 of Example 1) was added to 50 mL of unchlorinated domestic effluent supplied from an activated sludge treatment plant containing non-soluble fecal coliforms, enterococci and polio viruses. This solution was placed in a 100 mL beaker, exposed to visible light radiation (1500 μEm$^{-2}$s$^{-1}$) in a photoreactor equipped with an air-cooled halogen lamp (450 W) having a light spectrum similar to ordinary daylight (sunlight). The photoreactor was located in a cold room (5° C.) in order to keep the irradiated solution at 22°–24° C. Samples of the solution were taken after 10, 30 and 60 minutes of irradiation and checked, using colony forming units (CFU) for counting coliforms, fecal coliforms and enterococci in the effluents or platform forming units (PFU) for counting polioviruses, 1 LSc vaccine strain seeded in the effluents. The results are given in the following Table 1 and are compared to those obtained with methylene blue under the same conditions:

TABLE 1

| Microorganism | Sunlight exposure min | initial count | Compound 1 final count | Methylene blue final count |
|---|---|---|---|---|
| Coliforms | 10 | 20000 | 80 | 100 |
| (CFU/mL) | 30 | 20000 | 0.7 | 10 |
| Enterococci | 10 | 10000 | 0.1 | 1 |
| (CFU/mL) | 30 | 10000 | 0.08 | 0.2 |
| Polioviruses | 30 | 10000 | 50 | 275 |
| (PFU/mL) | 60 | 10000 | 0.4 | 50 |

EXAMPLE 10

Bioassay Determination

The procedure of Example 9 was repeated using 25μ of BDAP glutamate (compound 2 of Example 2) instead of BDAP p-toluenesulfonate. The results are given in the following Table 2 and are compared to those obtained with methylene blue under the same conditions:

TABLE 2

| Microorganism | Sunlight exposure min | initial count | Compound 2 final count | Methylene blue final count |
|---|---|---|---|---|
| Coliforms | 10 | 20000 | 85 | 100 |
| (CFU/mL) | 30 | 20000 | 1 | 10 |
| Enterococci | 10 | 10000 | 0.5 | 1 |
| (CFU/mL) | 30 | 10000 | 0.1 | 0.2 |
| Polioviruses | 30 | 10000 | 100 | 275 |
| (PFU/mL) | 60 | 10000 | 10 | 50 |

EXAMPLE 11

Bioassay Determination

The procedure of Example 9 was repeated using BDAP gluconate (compound 3 of Example 3) instead of BDAP p-toluenesulfonate. The results are given in the following Table 3 and are compared to those obtained with methylene blue under the same conditions:

TABLE 3

| Microorganism | Sunlight exposure min | initial count | Compound 3 final count | Methylene blue final count |
|---|---|---|---|---|
| Coliforms | 10 | 20000 | 100 | 100 |
| (CFU/mL) | 30 | 20000 | 10 | 10 |
| Enterococci | 10 | 10000 | 0.5 | 1 |
| (CFU/mL) | 30 | 10000 | 0.2 | 0.2 |
| Polioviruses | 30 | 10000 | 100 | 275 |
| (PFU/mL) | 60 | 10000 | 1 | 50 |

EXAMPLE 12

Bioassay Determination

The procedure of Example 9 was repeated using Compound Ia (Example 5) instead of BDAP p-toluenesulfonate. The results are given in the following Table 4 and are compared to those obtained with methylene blue under the same conditions:

TABLE 4

| Microorganism | Sunlight exposure min | initial count | Compound Ta final count | Methylene blue final count |
|---|---|---|---|---|
| Coliforms | 10 | 20000 | 80 | 100 |
| (CFU/mL) | 30 | 20000 | 0.7 | 10 |
| Enterococci | 10 | 10000 | 0.1 | 1 |
| (CFU/mL) | 30 | 10000 | 0.08 | 0.2 |

We claim:
1. 3,7-Disubstituted-phenothiazinium salts of the formula (I):

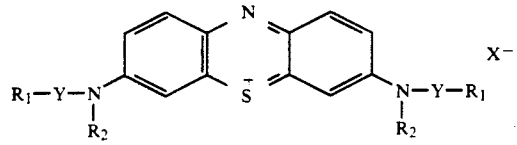

wherein:
either $R_1$ is a saccharide residue;
$R_2$ is alkyl, cycloalkyl, aryl, aralkyl or heterocyclyl, any alkyl or alkylene chain being optionally interrupted by one or more heteroatoms, and
Y is alkylene optionally substituted by alkyl, cycloalkyl, aryl or aralkyl; or
$R_1$ and $R_2$ are each methyl and Y is a bond; and when $R_1$ is a saccharide residue X is an anion selected from halogen, $R_3CO_2^-$, $R_3SO_3^-$ and $R_3OSO_3^-$, wherein $R_3$ is alkyl, cycloalkyl, aryl, aralkyl or heterocyclyl, and
when $R_1$ and $R_2$ are each methyl, X is an anion selected from $R_3SO_3^-$, $R_3OSO_3^-$ wherein $R_3$ is as defined above and $R_4CO_2^-$, wherein $R_4$ is an aldose or ketose residue, an N-protected α-amino acid residue or a ω-carboxy-α-amino acid residue.

2. A compound according to claim 1, wherein $R_1$ is glucosyl.

3. A compound according to claim 1, wherein $R_1$ is galactosyl.

4. A compound according to claim 1, wherein each of $R_1$ and $R_2$ is methyl.

5. 3,7-Bis(N-methyl-N-β-glucopyranosylethylamino)phenothiazin-5-ium bromide.

6. 3,7-Bis(N-methyl-N-β-galactopyranosylethylamino)phenothiazin-5-ium bromide.

7. 3,7-Bis(dimethylamino)phenothiazin-5-ium p-methylbenzenesulfonate.

8. 3,7-Bis(dimethylamino)phenothiazin-5-ium glutamate.

9. 3,7-Bis(dimethylamino)phenothiazin-5-ium gluconate.

10. A process for disinfecting aqueous effluents which comprises dissolving in said effluents about 1 to 4 ppm of a compound according to claim 1 and subjecting said effluent to irradiation with white light in the presence of air.

11. A process according to claim 10 wherein the salt is 3,7-bis(N-methyl-N-β-glucopyranosylethyl-amino)-phenothiazin-5-ium bromide.

12. A process according to claim 10 wherein the salt is 3,7-bis(N-methyl-N-β-galactopyranosylethylamino)-phenothiazin-5-ium bromide.

13. A process according to claim 10 wherein the salt is 3,7-bis(dimethylamino)phenothiazin-5-ium p-methylbenzenesulfonate.

14. A process according to claim 10 wherein the salt is 3,7-bis(dimethylamino)phenothiazin-5-ium glutamate.

15. A process according to claim 10 wherein the salt is 3,7-bis(dimethylamino)phenothiazin-5-ium gluconate.

* * * * *